United States Patent
Perron et al.

(10) Patent No.: US 6,617,292 B2
(45) Date of Patent: Sep. 9, 2003

(54) KERATINOUS WASHING COMPOSITION COMPRISING PARTICLES OF ALUMINUM OXIDE, AT LEAST ONE ANIONIC SURFACTANT AND AT LEAST ONE AMPHOTERIC OR NONIONIC SURFACTANT

(75) Inventors: Béatrice Perron, Jouy en Josas (FR); Serge Restle, Saint Prix (FR); Franck Giroud, Clichy (FR); Henri Samain, Bièvres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/955,026

(22) Filed: Sep. 19, 2001

(65) Prior Publication Data

US 2002/0055446 A1 May 9, 2002

(30) Foreign Application Priority Data

Sep. 20, 2000 (FR) .............................. 00 11994

(51) Int. Cl.⁷ ................................ A61K 7/50

(52) U.S. Cl. ................ 510/119; 510/121; 510/123; 510/125; 510/126; 510/508

(58) Field of Search ................ 510/119, 121, 510/122, 123, 125, 126, 508

(56) References Cited

U.S. PATENT DOCUMENTS 3,819,827 A    6/1974  Berger et al. ............ 424/70

FOREIGN PATENT DOCUMENTS

GB    2 124 245    2/1984

*Primary Examiner*—Necholus Ogden
(74) *Attorney, Agent, or Firm*—Steptoe & Johnson LLP; D. Douglas Price

(57) ABSTRACT

The present invention relates to a composition for washing keratinous materials which comprises, in a cosmetically acceptable aqueous medium, particles essentially consisting of aluminium oxide and having a mean primary size in numerical terms of less than 200 nm, at least one anionic surfactant and at least one amphoteric or nonionic surfactant. The invention also relates to a method for the cosmetic treatment of keratinous fibres, as well as a use of the composition according to the invention as a shampoo.

19 Claims, No Drawings

KERATINOUS WASHING COMPOSITION COMPRISING PARTICLES OF ALUMINUM OXIDE, AT LEAST ONE ANIONIC SURFACTANT AND AT LEAST ONE AMPHOTERIC OR NONIONIC SURFACTANT

The present invention relates to a composition for washing keratinous materials comprising particles essentially consisting of aluminium oxide, at least one anionic surfactant and at least one amphoteric or nonionic surfactant, to a method for the cosmetic treatment of keratinous fibres and to a use of the composition as a shampoo.

U.S. Pat. No. 3,819,827 by WELLA describes in particular hair-setting products comprising from 0.2 to 6% by weight of particles of aluminium oxide having a particle size of about 30 mμ, and from 1 to 4% by weight of polymers such as gum tragacanth, agar, pectin, vinyl polymers and basic polymers.

The applicant has found, surprisingly, that the use of particles essentially consisting of aluminium oxide and having a mean primary size in numerical terms of less than 200 nm, with a particular surfactant base comprising an anionic surfactant and an amphoteric or nonionic surfactant in washing compositions, made it possible to obtain good retention and a certain volume of the hair, that is to say a hairstyling effect. It is observed, moreover, that the keratinous fibres are hardened and straightened.

The subject of the present invention is therefore a washing composition comprising, in a cosmetically acceptable aqueous medium, particles essentially consisting of aluminium oxide and having a mean primary size in numerical terms of less than 200 nm, at least one anionic surfactant and at least one amphoteric or nonionic surfactant.

Another subject of the invention consists in a method for the cosmetic treatment of keratinous fibres using the composition according to the invention.

The subject of the invention is also a use of the composition according to the invention as a shampoo.

Other objectives, characteristics, aspects and advantages of the invention will emerge more clearly on reading the description and the various examples which follow.

According to the invention, the composition for washing keratinous materials comprises, in a cosmetically acceptable aqueous medium, particles essentially consisting of aluminium oxide and having a mean primary size in numerical terms of less than 200 nm, at least one anionic surfactant and at least one amphoteric or nonionic surfactant.

The expression "cosmetically acceptable aqueous medium" is understood to mean an aqueous medium which is compatible with keratinous materials such as the skin and the hair.

The expression "particles essentially consisting of aluminium oxide" is understood to mean particles consisting, at more than 90% by weight, of aluminium oxide.

For the purposes of the present invention, the expression "primary size of a particle" is understood to mean the maximum size which it is possible to measure between two diametrically opposite points of an individual particle. The size may be determined by transmission electron microscopy or from the measurement of the specific surface area by the BET method.

The mean primary size in numerical terms of the particles is preferably between 5 and 50 nm.

The particles of aluminium oxide according to the invention essentially consist of any optionally hydrated alumina such as, for example, boehmite.

The particles may have any shape such as, for example, the shape of a sphere, of flakes, of needles or of plates. Preferably, they are substantially spherical.

The particles of aluminium oxide may be used in the composition according to the invention in a quantity ranging from 0.01 to 20% by weight, preferably from 0.1 to 5% by weight, relative to the total weight of the washing composition of the invention.

As anionic surfactants which can be used in the present invention, there may be mentioned in particular salts, in particular alkali metal salts such as sodium salts, ammonium salts, amine salts, salts of amino alcohols or salts of alkaline-earth metals, for example, of magnesium, of the following types: alkyl sulphates, alkyl ether sulphates, alkyl amidoether sulphates, alkyl aryl polyether sulphates, monoglyceride sulphates; alkyl sulphonates, alkyl amide sulphonates, alkyl aryl sulphonates, α-olefin sulphonates, paraffin sulphonates; alkyl sulphosuccinates, alkyl ether sulphosuccinates, alkyl amide sulphosuccinates; alkyl sulphoacetates; acyl sarcosinates; and acyl glutamates, the alkyl and acyl groups of all these compounds comprising from 6 to 24 carbon atoms and the aryl group preferably denoting a phenyl or benzyl group. It is also possible to use esters of $C_6$–$C_{24}$ alkyl and of polyglycosidecarboxylic acids such as alkyl glucoside citrates, alkyl polyglycoside tartrates, alkyl polyglycoside sulphosuccinates; alkyl sulphosuccinamates, acyl isethionates and N-acyltaurates, the alkyl or acyl group of all these compounds comprising from 12 to 20 carbon atoms. Among the anionic surfactants which may be further used, there may also be mentioned acyl lactylates in which the acyl group comprises from 8 to 20 carbon atoms.

In addition, there may be further mentioned alkyl D-galactoside uronic acids and their salts such as polyoxyalkylenated ($C_6$–$C_{24}$)alkyl ether carboxylic acids, polyoxyalkylenated ($C_6$–$C_{24}$) alkyl ($C_6$–$C_{24}$) aryl ether carboxylic acids, polyoxyalkylenated ($C_6$–$C_{24}$)alkyl amido-ether carboxylic acids and their salts, in particular those comprising from 2 to 50 ethylene oxide groups, and mixtures thereof.

The anionic surfactants described above may be used alone or in the form of a mixture. The alkyl sulphates, alkyl ether sulphates and alkyl ether carboxylates and mixtures thereof are preferably used, in particular in the form of their alkali or alkaline-earth metal, ammonium, amine or amino alcohol salts.

The amphoteric surfactants which are suitable in the present invention may be in particular secondary or tertiary aliphatic amine derivatives in which the aliphatic group is a linear or branched chain comprising from 8 to 22 carbon atoms and containing at least one water-solubilizing anionic group such as, for example, a carboxylate, sulphonate, sulphate, phosphate or phosphonate group; there may also be mentioned ($C_8$–$C_{20}$)alkyl betaines, sulphobetaines, ($C_8$–$C_{20}$)alkyl amido ($C_6$–$C_8$)alkyl betaines or ($C_8$–$C_{20}$) alkyl amido ($C_6$–$C_8$)alkyl sulphobetaines; and mixtures thereof.

Among the amine derivatives, there may be mentioned the products marketed under the name MIRANOL®, as described in U.S. Pat. Nos. 2,528,378 and 2,781,354 and classified in the CTFA dictionary, 3rd edition, 1982, under the names Amphocarboxyglycinate and Amphocarboxypropionate having the respective structures (1) and (2).

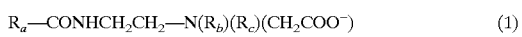

in which:

$R_a$ represents an alkyl group derived from an acid $R_a$-COOH present in hydrolysed copra oil, a heptyl, nonyl or undecyl group, $R_b$ represents a β-hydroxyethyl group, and
$R_c$ represents a carboxymethyl group; and

$$R_{a'}\text{—CONHCH}_2\text{CH}_2\text{—N(B)(C)} \qquad (2)$$

in which:
B represents —CH$_2$CH$_2$OX',
C represents —(CH$_2$)$_z$—Y', with z=1 or 2,
X' represents the group —CH$_2$CH$_2$—COOH or a hydrogen atom,
Y' represents —COOH or the group —CH$_2$—CHOH—SO$_3$H, $R_{a'}$ represents an alkyl group of an acid $R_{a'}$—COOH present in copra oil or in hydrolysed linseed oil, an alkyl group, in particular as C$_{17}$ and its isoform, or an unsaturated C$_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid or cocoamphodipropionic acid.

By way of example, there may be mentioned the cocoamphodiacetate marketed under the trade name MIRANOL® C2M concentrated by the company RHODIA.

The nonionic surfactants which are suitable in the invention are compounds well known per se (see in particular in this regard <<Handbook of Surfactants>> by M. R. PORTER, Blackie & Son publishers (Glasgow and London), 1991, pp. 116–178). Thus, they may be chosen in particular from alcohols, α-diols, (C$_1$–C$_{20}$)alkylphenols or polyethoxylated, polypropoxylated or polyglycerolated fatty acids, having a fatty chain comprising, for example, from 8 to 18 carbon atoms, it being possible for the number of ethylene oxide or propylene oxide groups to range in particular from 2 to 50 and it being possible for the number of glycerol groups to range in particular from 2 to 30. There may also be mentioned copolymers of ethylene and propylene oxide, condensates of ethylene and propylene oxide with fatty alcohols; polyethoxylated fatty amides preferably having from 2 to 30 mol of ethylene oxide, polyglycerolated fatty amides comprising on average 1 to 5 glycerol groups and in particular 1.5 to 4; polyethoxylated fatty amines preferably having 2 to 30 mol of ethylene oxide; ethoxylated fatty acid esters of sorbitan having from 2 to 30 mol of ethylene oxide; fatty acid esters of sucrose, fatty acid esters of polyethylene glycol, (C$_6$–C$_{24}$)alkyl polyglycosides, derivatives of N—(C$_6$–C$_{24}$)alkyl glucamine, amine oxides such as (C$_{10}$–C$_{14}$)alkylamine oxides or N—(C$_{10}$–C$_{14}$) acylaminopropylmorpholine oxides; and mixtures thereof.

Among the nonionic surfactants cited above, (C$_5$–C$_{24}$) alkyl polyglycosides are preferably used. The anionic surfactants, the amphoteric surfactants and the nonionic surfactants are used in the composition of the present invention in a total quantity of between 4 and 50% by weight, preferably between 5 and 35% by weight and better still between 8 and 25% by weight relative to the total weight of the composition.

The composition according to the invention may also comprise, in addition, at least one treatment agent which is soluble or insoluble in the cosmetically acceptable aqueous medium.

The treatment agents are compounds which are well known and which are generally used in the art. By way of example, there may be mentioned in particular saccharides, oligosaccharides, polysaccharides which are hydrolysed or otherwise, modified or otherwise; amino acids; oligopeptides, peptides; proteins which are hydrolysed or otherwise and modified or otherwise; branched or unbranched fatty acids and alcohols; animal, vegetable or mineral waxes; ceramides and pseudoceramides; hydroxylated organic acids; UV-screening agents; antioxidants and anti-free radical agents; chelators; antidandruff agents; seborrhoea-regulating agents; soothing agents; cationic surfactants; cationic and amphoteric polymers; organomodified or non-organomodifed silicones; mineral, vegetable, animal or synthetic oils; polyisobutenes and poly(α-olefins); esters; soluble or dispersed anionic polymers; soluble or dispersed nonionic polymers; and mixtures thereof.

These treatment agents are used in the composition in an effective quantity, that is to say in a quantity which makes it possible to obtain the treatment effects sought by persons skilled in the art.

The cosmetically acceptable aqueous medium may consist solely of water or of a mixture of water and a cosmetically acceptable solvent such as a C$_1$–C$_4$ lower alcohol such as ethanol, isopropanol, tert-butanol, n-butanol; alkylene glycols such as propylene glycol, polyol ethers; C$_5$–C$_{10}$ alkanes; acetone, methyl ethyl ketone; C$_1$–C$_4$ alkyl acetates such as methyl acetate, ethyl acetate, butyl acetate; dimethoxyethane, diethoxyethane; and mixtures thereof.

The pH of the compositions of the invention is between 4 and 8, preferably between 5 and 7.

The compositions according to the invention may also contain, in addition, additives such as associative or nonassociative, anionic, amphoteric, zwitterionic, nonionic or cationic, natural or synthetic polymeric thickeners, nonpolymeric thickeners such as acids or electrolytes, pearlescent agents, opacifying agents, organic solvents, perfumes, colorants, organic particles, preservatives and pH-stabilizing agents.

Persons skilled in the art will be careful to choose the optional additives and their quantity so that they do not damage the properties of the compositions of the present invention.

These additives are present in the composition according to the invention in a quantity ranging from 0 to 20% by weight relative to the total weight of the composition.

The compositions may be provided in the form of liquids which are fluid or thickened, gels, creams, mousses, water-in-oil (W/O), oil-in-water (O/W) emulsions or multiple emulsions.

They may be used, for example, as shampoos, rinse-out treatments, deep treatment masks, lotions or creams for treating the scalp.

The present invention also relates to a method of cosmetic treatment which consists in applying an effective quantity of a composition as described above to the keratinous fibres, and in rinsing after an optional exposure time.

According to a preferred embodiment of the invention, the composition may be used as a shampoo.

The following examples illustrate the present invention and should not be considered in any way as limiting the invention.

EXAMPLES

Shampoos of the following compositions A and B were prepared from the ingredients indicated in the table below. The quantities are indicated in % by weight relative to the total weight of the composition.

| Composition | A | B |
| --- | --- | --- |
| Aluminium oxide[1] | 0.5 | 0.5 |
| Sodium lauryl ether sulphate (2.2 mol of ethylene oxide) containing 26% of active substance | 47.5 | 47.5 |
| Sodium cocoamphodiacetate containing 38% of active substance | 6.6 | 6.6 |
| JR400 (AMERCHOL) | — | 0.5 |
| Water | qs 100 | qs 100 |
| pH | 6.5 | 6.5 |

[1]having a mean primary particle size in numerical terms of 13 nm, sold under the name ALUIMINIUMOXID C by the company DEGUSSA-HULS.

Compositions A and B according to the invention are applied to the hair, rinsed and the hair is dried.

Strengthening of the keratinous fibres is observed and the hair can be styled better.

What is claimed is:

1. A composition for washing keratinous materials, comprising, in a cosmetically acceptable aqueous medium, particles consisting essentially of aluminium oxide and having a mean primary size of between 5 nm and 200 nm, at least one anionic surfactant and at least one amphoteric or nonionic surfactant, wherein the total quantity of surfactants is from 4 to 50% by weight relative to the total weight of the composition.

2. The composition according to claim 1, wherein the mean primary size of the particles is between 5 and 50 nm.

3. The composition according to claim 1, wherein the aluminium oxide is alumina or hydrated alumina.

4. The composition according to claim 3, wherein the aluminium oxide is boehmite.

5. The composition according to claim 1, wherein the particles are present in a concentration of 0.01 to 20% by weight relative to the total weight of the composition.

6. The composition according to claim 5, wherein the particles are present in a concentration of 0.1 to 5% by weight relative to the total weight of the composition.

7. The composition according to claim 1, wherein the anionic surfactant is a salt of an alkyl sulphate, an alkyl ether sulphate, an alkyl amidoether sulphate, an alkyl aryl polyether sulphate, a monoglyceride sulphate; an alkyl sulphonate, an alkyl amide sulphonate, an alkyl aryl sulphonate, an α-olefin sulphonate, a paraffin sulphonate; an alkyl sulphosuccinate, an alkyl ether sulphosuccinate, an alkyl amide sulphosuccinate; an alkyl sulphoacetate; an acyl sarcosinate; an acyl glutamate, the alkyl and acyl groups comprising from 6 to 24 carbon atoms and the aryl group denoting a phenyl or benzyl group; an ester of $C_6$–$C_{24}$ alkyl or of polyglycosidecarboxylic acid; an alkyl sulphosuccinamate, an acyl isethionate or an N-acyltaurate, the alkyl or acyl group comprising from 12 to 20 carbon atoms; an acyl lactylate in which the acyl group comprises from 8 to 20 carbon atoms; an alkyl D-galactoside uronic acid or its salt, a polyoxyalkylenated ($C_6$–$C_{24}$)alkyl ether carboxylic acid, a polyoxyalkylenated ($C_6$–$C_{24}$)alkyl ($C_6$–$C_{24}$)aryl ether carboxylic acid, polyoxyalkylenated ($C_6$–$C_{24}$)alkyl amidoether carboxylic acid or their salts; or mixtures thereof.

8. The composition according to claim 7, wherein the anionic surfactant is an alkyl sulphate, an alkyl ether sulphate or alkyl ether carboxylate or mixture thereof in the form of an alkali metal, alkaline-earth metal, amine, ammonium or amino alcohol salt.

9. The composition according to claim 1, wherein the amphoteric surfactant is a secondary or tertiary aliphatic amine derivative in which the aliphatic group is a linear or branched chain comprising from 8 to 22 carbon atoms and containing at least one water-solubilizing anionic group; a ($C_8$–$C_{20}$)alkyl betaine, a sulphobetaine, a ($C_8$–$C_{20}$)alkyl amido ($C_6$–$C_8$)alkyl betaine or a ($C_6$–$C_{20}$)alkyl amido ($C_6$–$C_8$)alkyl sulphobetaine; or mixtures thereof.

10. The composition according to claim 1, wherein the nonionic surfactant is an alcohol, an alpha-diol, a ($C_1$–$C_{20}$) alkylphenol or a ($C_8$–$C_{18}$)polyethoxylated, polypropoxylated or polyglycerolated fatty acid, the number of ethylene oxide or propylene oxide groups ranging from 2 to 50 and the number of glycerol groups ranging from 2 to 30, a copolymer of ethylene and propylene oxide, a condensate of ethylene and propylene oxide with a fatty alcohol; a polyethoxylated fatty amide having from 2 to 30 mol of ethylene oxide, a polyglycerolated fatty amide comprising on average 1 to 5 glycerol groups; a polyethoxylated fatty amine having 2 to 30 mol of ethylene oxide; an ethoxylated fatty acid ester of sorbitan having from 2 to 30 mol of ethylene oxide; a fatty acid ester of sucrose, a fatty acid ester of polyethylene glycol, a ($C_6$–$C_{24}$)alkyl polyglycoside, a derivative of N-($C_6$–$C_{24}$)alkyl glucamine, an amine oxide; or mixtures thereof.

11. The composition according to claim 1, wherein surfactants are present in a quantity of between 8 and 25% by weight relative to the total weight of the composition.

12. The composition according to claim 1, wherein the composition further comprises at least one treatment agent which is soluble or insoluble in the cosmetically acceptable aqueous medium.

13. The composition according to claim 12, wherein the treatment agent is a saccharide, an oligosaccharide, a polysaccharide which is hydrolyzed or unhydrolyzed, modified or unmodified; an amino acid; an oligopeptide, a peptide; a protein which is hydrolyzed or unhydrolyzed or modified or unmodified; a branched or unbranched fatty acid or alcohol; an animal, vegetable or mineral wax; a ceramide or pseudoceramide; a hydroxylated organic acid; a UV-screening agent; an antioxidant or anti-free radical agent; a chelator; an antidandruff agent; a seborrhoea-regulating agent; a soothing agent; a cationic surfactant; a cationic or amphoteric polymer; an organomodified or non-organomodified silicone; a mineral, vegetable, animal or synthetic oil; a polyisobutene or poly(α-olefin); an ester; a soluble or dispersed anionic polymer; a soluble or dispersed nonionic polymer; or mixtures thereof.

14. The composition according to claim 13, wherein the treatment agent is a cationic or amphoteric polymer.

15. The composition according to claim 1, wherein the cosmetically acceptable aqueous medium consists solely of water or of a mixture of water and of a cosmetically acceptable solvent.

16. The composition according to claim 15, wherein the cosmetically acceptable solvent is a $C_1$–$C_4$ lower alcohol, an alkylene glycol, a $C_5$–$C_{10}$ alkane, acetone, methyl ethyl ketone, a $C_1$–$C_4$ alkyl acetate, dimethoxyethane, diethoxyethane or mixtures thereof.

17. The composition according to claim 1, wherein the composition further comprises an associative or nonassociative, anionic, amphoteric, zwitterionic, nonionic or cationic, natural or synthetic polymeric thickener, a nonpolymeric thickener, a pearlescent agent, an opacifying agent, a perfume, a colorant, an organic particle, a preservative or a pH-stabilizing agent.

18. The composition of claim 1, wherein the composition is a shampoo.

19. A method for the cosmetic treatment of keratinous fibres, comprising applying a washing composition to the keratinous fibres, and rinsing the keratinous fibres, the washing composition comprising, in a cosmetically acceptable aqueous medium, particles consisting essentially of aluminium oxide and having a mean primary size of between 5 nm and 200 nm, at least one anionic surfactant and at least one amphoteric or nonionic surfactant.

* * * * *